(12) United States Patent
Guan et al.

(10) Patent No.: US 7,889,347 B2
(45) Date of Patent: Feb. 15, 2011

(54) SURFACE PLASMON RESONANCE SPECTROMETER WITH AN ACTUATOR DRIVEN ANGLE SCANNING MECHANISM

(75) Inventors: Hann-Wen Guan, Bothell, WA (US); Shuxin Cong, Lynnwood, WA (US)

(73) Assignee: Plexera LLC, Woodinville, WA (US)

( * ) Notice: Subject to any disclaimer, the term of this patent is extended or adjusted under 35 U.S.C. 154(b) by 295 days.

(21) Appl. No.: 11/562,197

(22) Filed: Nov. 21, 2006

(65) Prior Publication Data
US 2007/0222996 A1 Sep. 27, 2007

Related U.S. Application Data

(60) Provisional application No. 60/738,880, filed on Nov. 21, 2005.

(51) Int. Cl.
G01J 4/00 (2006.01)
(52) U.S. Cl. ............. 356/445; 356/369; 356/237.2
(58) Field of Classification Search .......... 356/445
See application file for complete search history.

(56) References Cited
U.S. PATENT DOCUMENTS

| 3,105,902 | A | * | 10/1963 | Ostrofsky et al. ............ 378/49 |
| 3,751,587 | A | | 8/1973 | Insler |
| 3,891,507 | A | | 6/1975 | Breuer |
| 3,990,850 | A | | 11/1976 | Friedman |
| 4,038,030 | A | | 7/1977 | Albright |
| 4,148,057 | A | | 4/1979 | Jesse |
| 4,375,025 | A | | 2/1983 | Carlson |
| 4,585,931 | A | | 4/1986 | Duncan |
| 4,638,144 | A | | 1/1987 | Latta |
| 4,707,722 | A | | 11/1987 | Folk |
| 4,719,502 | A | | 1/1988 | Ikeya |
| 4,753,863 | A | | 6/1988 | Spanjer |
| 4,789,804 | A | | 12/1988 | Karube |
| 4,861,620 | A | | 8/1989 | Azuma |
| 4,945,045 | A | | 7/1990 | Forrest |

(Continued)

FOREIGN PATENT DOCUMENTS

DE 10064146 7/2002

(Continued)

OTHER PUBLICATIONS

Brockman et al., "Surface Plasmon Resonance Imaging Measurements of Ultrathin Organic Films", Ann. Rev. Phys. Chem., 2000, 51:41-63.

(Continued)

Primary Examiner—Gregory J Toatley
Assistant Examiner—Rebecca C Slomski
(74) Attorney, Agent, or Firm—Sci-Law Strategies, PC

(57) ABSTRACT

Instruments and methods relating to surface plasmon imaging are described. An instrument comprises a semi-circular rail and a driving mechanism. The driving mechanism is attached to a light source mount and a detector mount, and both the light source mount and the detector mount are attached to the semi-circular rail with connectors. Each connector allows the light source mount and detector mount to slide along the rail. The synchronous movement of the light source mount and the detector mount changes the angle of incidence of a light beam from the light source with respect to the plane of the sample surface on the sample stage.

25 Claims, 4 Drawing Sheets

U.S. PATENT DOCUMENTS

| | | | |
|---|---|---|---|
| 4,945,204 A | 7/1990 | Nakamura | |
| 4,997,278 A * | 3/1991 | Finlan et al. | 356/128 |
| 5,030,551 A | 7/1991 | Herren | |
| 5,068,124 A | 11/1991 | Batey | |
| 5,078,855 A | 1/1992 | Mochizuki | |
| 5,089,112 A | 2/1992 | Skotheim | |
| 5,104,619 A | 4/1992 | de Castro | |
| 5,116,481 A | 5/1992 | Ozawa | |
| 5,157,412 A | 10/1992 | Kleinschmick | |
| 5,192,507 A | 3/1993 | Taylor | |
| 5,200,051 A | 4/1993 | Cozzette | |
| 5,206,280 A | 4/1993 | Williams | |
| 5,242,828 A | 9/1993 | Bergstrom | |
| 5,246,846 A | 9/1993 | Pittner | |
| 5,262,470 A | 11/1993 | Shimotsuma | |
| 5,268,305 A | 12/1993 | Ribi | |
| 5,313,264 A | 5/1994 | Ivarsson | |
| 5,329,090 A | 7/1994 | Woelki | |
| 5,346,802 A | 9/1994 | Ohbachi | |
| 5,357,077 A | 10/1994 | Tsuruta | |
| 5,368,712 A | 11/1994 | Tomich | |
| 5,373,039 A | 12/1994 | Sakai | |
| 5,401,378 A | 3/1995 | King | |
| 5,405,783 A | 4/1995 | Pirrung | |
| 5,413,629 A | 5/1995 | Yasui | |
| 5,415,838 A | 5/1995 | Rieger | |
| 5,436,161 A | 7/1995 | Bergstrom | |
| 5,436,170 A | 7/1995 | Cornell | |
| 5,445,923 A | 8/1995 | Takahashi | |
| 5,445,934 A | 8/1995 | Fodor | |
| 5,474,796 A | 12/1995 | Brennan | |
| 5,478,756 A | 12/1995 | Gizeli | |
| 5,485,277 A | 1/1996 | Foster | |
| 5,491,097 A | 2/1996 | Ribi | |
| 5,492,840 A | 2/1996 | Malmqvist | |
| 5,512,131 A | 4/1996 | Kumar | |
| 5,514,501 A | 5/1996 | Tarlov | |
| 5,527,711 A | 6/1996 | Tom-Moy | |
| 5,536,822 A | 7/1996 | Haystead | |
| 5,567,301 A | 10/1996 | Stetter | |
| 5,571,568 A | 11/1996 | Ribi | |
| 5,580,794 A | 12/1996 | Allen | |
| 5,622,872 A | 4/1997 | Ribi | |
| 5,624,537 A | 4/1997 | Turner | |
| 5,629,790 A | 5/1997 | Neukermans | |
| 5,637,201 A | 6/1997 | Raguse | |
| 5,688,642 A | 11/1997 | Chrisey | |
| 5,693,477 A | 12/1997 | Cornell | |
| 5,707,502 A | 1/1998 | McCaffrey | |
| 5,716,778 A | 2/1998 | Weng | |
| 5,719,060 A | 2/1998 | Hutchens | |
| 5,723,345 A | 3/1998 | Yamauchi | |
| 5,736,410 A | 4/1998 | Zarling | |
| 5,741,409 A | 4/1998 | Raguse | |
| 5,753,093 A | 5/1998 | Raguse | |
| 5,756,355 A | 5/1998 | Lang | |
| 5,783,054 A | 7/1998 | Raguse | |
| 5,798,030 A | 8/1998 | Raguse | |
| 5,824,483 A | 10/1998 | Houston | |
| 5,834,224 A | 11/1998 | Ruger | |
| 5,844,099 A | 12/1998 | Stahl | |
| 5,846,842 A | 12/1998 | Herron | |
| 5,922,594 A | 7/1999 | Lof | |
| 5,922,617 A | 7/1999 | Wang | |
| 5,938,595 A | 8/1999 | Glass | |
| 5,942,388 A | 8/1999 | Willner | |
| 5,955,379 A | 9/1999 | Lennox | |
| 5,985,377 A | 11/1999 | Corbet | |
| 6,020,208 A | 2/2000 | Hutchens | |
| 6,027,942 A | 2/2000 | Hutchens | |
| 6,040,193 A | 3/2000 | Winkler | |
| 6,054,270 A | 4/2000 | Southern | |
| 6,074,616 A | 6/2000 | Buechler | |
| 6,096,825 A | 8/2000 | Garnier | |
| 6,101,946 A | 8/2000 | Martinsky | |
| 6,113,992 A | 9/2000 | Corbet | |
| 6,146,593 A | 11/2000 | Pinkel | |
| 6,150,147 A | 11/2000 | Goldberg | |
| 6,165,335 A | 12/2000 | Lennox | |
| 6,197,599 B1 | 3/2001 | Chin | |
| 6,217,949 B1 | 4/2001 | Corbet | |
| 6,218,111 B1 | 4/2001 | Southern | |
| 6,218,194 B1 | 4/2001 | Lyndin | |
| 6,219,138 B1 | 4/2001 | Swanson | |
| 6,225,047 B1 | 5/2001 | Hutchens | |
| 6,225,625 B1 | 5/2001 | Pirrung | |
| 6,232,066 B1 | 5/2001 | Felder | |
| 6,245,590 B1 | 6/2001 | Wine | |
| 6,261,776 B1 | 7/2001 | Pirrung | |
| 6,291,155 B1 | 9/2001 | Raguse | |
| 6,291,183 B1 | 9/2001 | Pirrung | |
| 6,309,831 B1 | 10/2001 | Goldberg | |
| 6,322,970 B1 | 11/2001 | Little | |
| 6,329,209 B1 | 12/2001 | Wagner | |
| 6,340,597 B1 | 1/2002 | Svorc | |
| 6,346,413 B1 | 2/2002 | Fodor | |
| 6,362,912 B1 | 3/2002 | Lewis | |
| 6,379,929 B1 | 4/2002 | Burns | |
| 6,380,365 B1 | 4/2002 | Akerstrom | |
| 6,399,365 B2 | 6/2002 | Besemer | |
| 6,406,921 B1 | 6/2002 | Wagner | |
| 6,416,952 B1 | 7/2002 | Pirrung | |
| 6,421,164 B2 * | 7/2002 | Tearney et al. | 359/287 |
| 6,433,907 B1 | 8/2002 | Lippert | |
| 6,447,723 B1 | 9/2002 | Schermer | |
| 6,448,065 B2 | 9/2002 | Laugharn | |
| 6,448,089 B1 | 9/2002 | Vuong | |
| 6,461,490 B1 | 10/2002 | Lennox | |
| 6,472,179 B2 | 10/2002 | Stahl | |
| 6,478,939 B1 | 11/2002 | Lennox | |
| 6,482,593 B2 | 11/2002 | Walt | |
| 6,485,918 B1 | 11/2002 | Schermer | |
| 6,489,106 B1 | 12/2002 | Shivashankar | |
| 6,491,871 B1 | 12/2002 | Fodor | |
| 6,545,758 B1 | 4/2003 | Sandstrom | |
| 6,548,171 B1 | 4/2003 | Barbera-Guillem | |
| 6,558,623 B1 | 5/2003 | Ganz | |
| 6,565,813 B1 | 5/2003 | Garyantes | |
| 6,569,385 B1 | 5/2003 | Little | |
| 6,576,424 B2 | 6/2003 | Fodor | |
| 6,576,426 B2 | 6/2003 | Southern | |
| 6,583,193 B2 | 7/2003 | Yguerabide | |
| 6,600,031 B1 | 7/2003 | Fodor | |
| 6,610,482 B1 | 8/2003 | Fodor | |
| 6,733,977 B2 | 5/2004 | Besemer | |
| 6,785,433 B2 | 8/2004 | Tiefenthaler | |
| 6,787,368 B1 | 9/2004 | Wong | |
| 6,789,040 B2 | 9/2004 | Kaushikkar | |
| 6,800,453 B2 | 10/2004 | Labaer | |
| 6,806,361 B1 | 10/2004 | Kajisa | |
| 6,999,175 B2 | 2/2005 | Ivarsson | |
| 6,862,094 B2 | 3/2005 | Johansen | |
| 6,870,627 B2 | 3/2005 | Elkind | |
| 6,902,705 B1 | 6/2005 | Caillat | |
| 6,911,344 B1 | 6/2005 | Reichert | |
| 6,980,294 B2 | 12/2005 | Namba | |
| 7,041,208 B2 | 5/2006 | Staats | |
| 7,081,954 B2 | 7/2006 | Sandstrom | |
| 7,084,980 B2 | 8/2006 | Jones | |
| 7,126,688 B2 | 10/2006 | Rassman | |
| 7,251,085 B2 | 7/2007 | Bahatt | |
| 7,312,069 B2 * | 12/2007 | Ban et al. | 435/287.2 |
| 7,319,046 B2 | 1/2008 | Misiakos | |
| 7,463,358 B2 | 12/2008 | Wolf | |

| | | | |
|---|---|---|---|
| 2002/0024495 A1 | 2/2002 | Lippert | |
| 2002/0044893 A1 | 4/2002 | Corn | |
| 2002/0068813 A1 | 6/2002 | Dragic | |
| 2002/0127565 A1 | 9/2002 | Cunningham | |
| 2002/0140938 A1 | 10/2002 | Naya | |
| 2002/0197729 A1 | 12/2002 | Tsuzuki | |
| 2003/0082820 A1 | 5/2003 | Perbost | |
| 2003/0100004 A1 | 5/2003 | Kurz | |
| 2003/0107741 A1 | 6/2003 | Pyo | |
| 2003/0143576 A1 | 7/2003 | Chao | |
| 2004/0008345 A1 | 1/2004 | Nurmikko | |
| 2004/0014946 A1 | 1/2004 | Chao | |
| 2004/0043384 A1 | 3/2004 | Oleinikov | |
| 2004/0048311 A1 | 3/2004 | Ault-Riche | |
| 2004/0067597 A1 | 4/2004 | Datwani | |
| 2004/0161748 A1 | 8/2004 | He | |
| 2004/0174518 A1* | 9/2004 | Naiki et al. | 356/237.2 |
| 2004/0198637 A1 | 10/2004 | Schulz | |
| 2004/0214233 A1 | 10/2004 | Lubman | |
| 2004/0248144 A1 | 12/2004 | Mir | |
| 2004/0258832 A1 | 12/2004 | Barklund | |
| 2005/0002085 A1 | 1/2005 | Matsui | |
| 2005/0014179 A1 | 1/2005 | Karlsson | |
| 2005/0046848 A1 | 3/2005 | Cromwell | |
| 2005/0095577 A1 | 5/2005 | Yang | |
| 2005/0200845 A1* | 9/2005 | Nabatova-Gabain et al. | 356/369 |
| 2006/0091051 A1 | 5/2006 | Takada | |
| 2006/0134669 A1 | 6/2006 | Casasanta | |
| 2006/0154320 A1 | 7/2006 | Zuk | |
| 2006/0187459 A1 | 8/2006 | Ok | |
| 2006/0234265 A1 | 10/2006 | Richey | |
| 2007/0009198 A1 | 1/2007 | Petcavich | |
| 2007/0059817 A1 | 3/2007 | Aoyagi | |
| 2007/0081163 A1 | 4/2007 | Liang | |
| 2007/0122314 A1 | 5/2007 | Strand | |
| 2007/0128455 A1 | 6/2007 | Wolf | |
| 2007/0139653 A1 | 6/2007 | Guan | |
| 2007/0140918 A1 | 6/2007 | Yin | |
| 2007/0222996 A1 | 9/2007 | Guan | |
| 2009/0060786 A1 | 3/2009 | Kim | |
| 2009/0060787 A1 | 3/2009 | Kim | |

FOREIGN PATENT DOCUMENTS

| | | |
|---|---|---|
| WO | WO 93/15110 | 8/1993 |
| WO | WO 95/31480 | 11/1995 |
| WO | WO 96/02830 | 2/1996 |
| WO | WO 96/09547 | 3/1996 |
| WO | WO 97/07593 | 1/1997 |
| WO | WO 97/41424 | 1/1997 |
| WO | WO 97/41425 | 1/1997 |
| WO | WO 97/12988 | 4/1997 |
| WO | WO 02/052260 | 7/2002 |

OTHER PUBLICATIONS

Bogoyevitch et al., "Peptide inhibitors of protein kinases-discovery, characterisation and use", Biochim. Biophys. Acta, 2005, 1754: 79-99.

Eddings et al., "High throughput in situ Biomolecule Analysis Integrating a 3-D Microfluidic Flow Cell Array and SPR Microscopy" Department of Engineering, Chemistry and Mechanical Engineering, University of Utah.

Hines et al., "Bisubstrate analog probes for the insulin receptor protein kinase: Molecular yardsticks for analyzing catalytic mechanism and inhibitor design", Bioorg. Chem., 2005, 33:285-297.

Hu, J.C., et al., "Sequence Requirements for Coiled-Coils: Analysis with .lambda. Repressor-GCN4 Leucine Zipper Fusions" Science 250:1400-1403 (1990).

Hyun et al., "Enzymatic Nanolithography of a self assembled Oligionucleotide Monolayer on Gold", J. Am Chem. Soc., 2004, 126:4770-4771.

Komatsu, et al., "SPR sensor signal amplification based on dye-doped polymer particles" Sci. Tech. Adv. Mater., 2006 7:150-155.

Mitchell et al., "Sensitivity enhancement of surface plasmon resonance biosensing of small molecules" Anal Biochem, 2005, 343:125-135.

Qi et al., "Determination of the Bioavailability of Biotin Conjugated onto Shell Cross-Linked (SCK) Nanoparticles", J. Am. Chem. Soc., 2004 126:6599-6607.

Ramachandran et al., "Self-assembling protein microarrays", Science, 2004, 305:86-90.

Severs and Schasfoort, "Enhanced Surface Plasmon Resonance Inhibition Test (ESPRIT) using latex particles", Biosens. Bioelectron., 1993, 8:365-370.

Shen et al., "Protein kinase structure and function analysis with chemical tools" Biochim. Biophys. Acta, 2005, 1754:65-78.

"Surface Plasmon Resonance (SPR)", BMS, http://www.bmskorea.co.kr/bms_Product/bms_Product_Main.aspx?sec=detail&num=28211, printed Nov. 15, 2005, 6 pages.

Wink et al., "Liposome-Mediated Enhancement of the Sensitivity in Immunoassays of Proteins and Peptides in Surface Plasmon Resonance Spectrometry" Anal. Chem., 1998, 70:827-832.

International Search Report dated Jul. 3, 2008, Application No. PCT/US06/44957.

International Search Report dated May 10, 2007, Application No. PCT/US06/22123.

International Search Report dated Nov. 10, 2008, Application No. PCT/US08/74865.

* cited by examiner

SURFACE PLASMON RESONANCE SPECTROMETER WITH AN ACTUATOR DRIVEN ANGLE SCANNING MECHANISM

RELATED APPLICATIONS

This application claims priority under 35 USC §119(e) to U.S. Patent Application Ser. No. 60/738,880, filed on Nov. 21, 2005, the entire contents of which are hereby incorporated by reference.

TECHNICAL FIELD

This invention relates to scientific instruments and methods, and more particularly to surface plasmon resonance spectroscopy.

BACKGROUND

All patents, patent applications, and publications cited within this application are incorporated herein by reference to the same extent as if each individual patent, patent application or publication was specifically and individually incorporated by reference.

Surface Plasmon Resonance (SPR) spectroscopy is a powerful method capable of detecting molecular binding events at the nanometer scale by detecting changes in the effective refractive index or thickness of an adsorbed layer on or near an SPR active surface. When light is reflected from an SPR active medium at an angle greater than the critical angle, incident photons can generate surface plasmons. This phenomenon can be observed as a function of the reflected light intensity. The spatial difference of contrast can be acquired in an image format by employing a CCD camera as a detection system, namely SPR microscopy (SPRM).

Typically, SPR microscopy utilizes an angle of incidence of the irradiating beam at the prime SPR angle so that the system is conditioned to operate at its maximum linear response region. The procedure then involves rotating both sample and/or the detector and light source to establish the optimum optical pass configuration. Fine resolution rotation tables or linear diode arrays have been employed to provide the angular scanning function to obtain the SPR reflecting signal dip. Fixed wavelength, coherent angle scanning SPR employing dual rotation tables generally involves instruments having the optical pass configured in the horizontal plane. The physical size required for rotation stages offering fine resolution and providing enough torque to support the swing arms that hold either light source and/or detector gives the SPR instrument a large footprint. Thus, there is a need for an SPR instrument having a reduced footprint that allows SPR angle scanning.

SUMMARY

One embodiment is an SPR imager comprising a semicircular rail and a driving mechanism, wherein the driving mechanism is attached to a light source mount and a detector mount, and wherein both the light source mount and the detector mount are attached to the semi-circular rail with connectors, each connectors allowing the light source mount and detector mount to slide along the rail. Referring to FIG. 1, one embodiment is an instrument, comprising: a semicircular rail (2); a sample stage for receiving a sample (14), the sample stage forming a plane; a light source mount (8) on the rail (2); a light source (8a) on the light source mount (8); a detector mount (10) on the rail (2); a detector (10a) on the detector mount (10), wherein the light source mount (8) and the detector mount (10) move synchronously along the rail (2) in opposite directions (11a, 11b). The synchronous movement of the light source mount (8) and the detector mount (10) changes the angle of incidence of a light beam (12) from the light source (8a) with respect to the plane of the sample surface on the sample stage (14).

In another embodiment, the instrument further comprises a driving mechanism that comprises, referring to FIG. 2: a driving bridge (3) having a first pivot point (4a) and a second pivot point (6a); a first swing arm (4) with a first end (4b) and a second end (4c), the first end (4b) being connected to the driving bridge (3) through the first pivot point (4a); and a second swing arm (6) with a first end (6b) and a second end (6c), the first end (6b) being connected to the driving bridge (3) through the second pivot point (6a), wherein the second end (4c) of the first swing arm (4) is connected to a pivot point on the light source mount (8b) and the second end (6c) of the second swing arm (6) is connected to a pivot point on the detector mount (10b). Referring to FIGS. 2 and 3, when the driving bridge (3) moves along a path (15) substantially perpendicular to the plane of the sample stage, the light source mount (8) and the detector mount (10) move in opposite directions (11a and 11b). Using a single actuator to move the driving mechanism significantly reduces the instrument's physical size and mechanical complexity needed when, for example, dual rotation tables are used.

Another embodiment is a method, comprising: 1) providing a light source, a detector, and a sample, wherein the light source generates a light beam; 2) directing the light beam at the sample to form and angle of incidence between the light beam and the sample; and 3) moving the light source and the detector synchronously by sliding the light source and detector in opposite directions along a semicircular rail, thereby modifying the angle of incidence. In another embodiment, the sample is a microarray comprising gold and the light beam generates surface plasmon resonance at the gold surface.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

Figure 1:
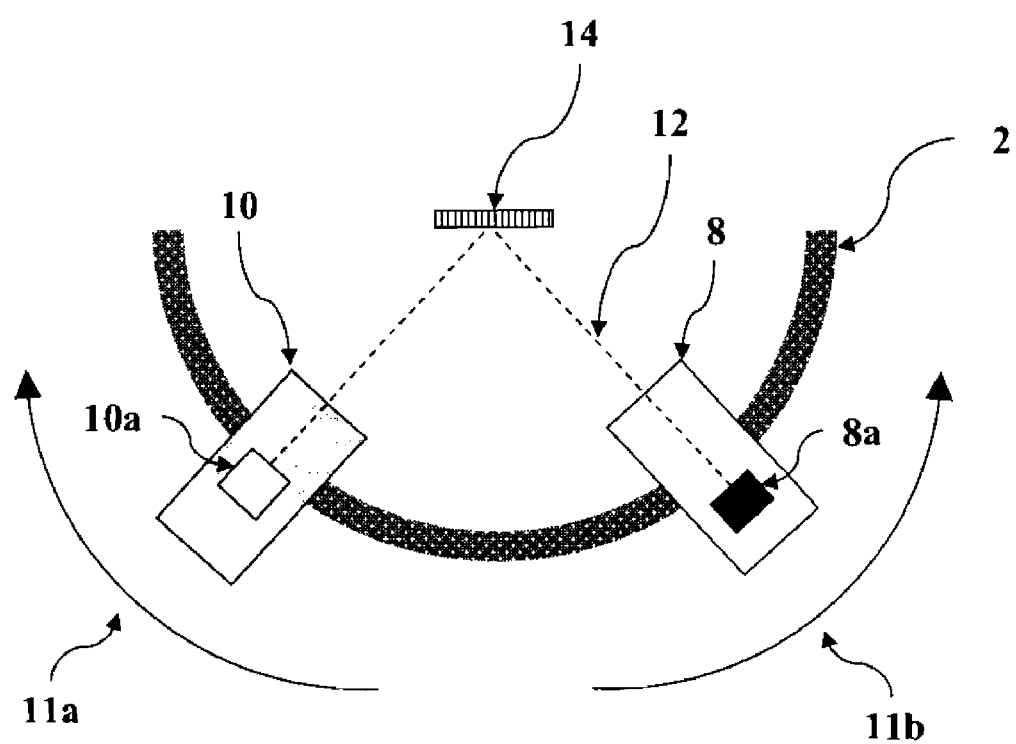
FIG. 1 illustrates one embodiment.

Referring to FIG. 1, one embodiment is an instrument, comprising: a semicircular rail (2); a sample stage for receiving a sample (14), the sample stage (14) forming a plane on which a sample may be placed; a light source mount (8) on the rail (2); a light source (8a) on the light source mount (8); a detector mount (10) on the rail (2); a detector (10a) on the detector mount (10), wherein the light source mount (8) and the detector mount (10) move synchronously along the rail (2) in opposite directions (denoted by arrows 11a and 11b). The synchronous movement of the light source mount (8) and the detector mount (10) changes the angle of incidence of a light beam (12) from the light source (8*a*) with respect to the plane of the sample surface on the sample stage (14). The sample stage (14) may be used for a microarray sample comprising gold, for example. The sample stage (14) may further include a microfluidic flow cell for supplying a liquid analyte to the surface of the microarray, and temperature regulator that may be used to influence instrument sensitivity by suppressing thermally induced sample changes in refractive index.

Figure 2:
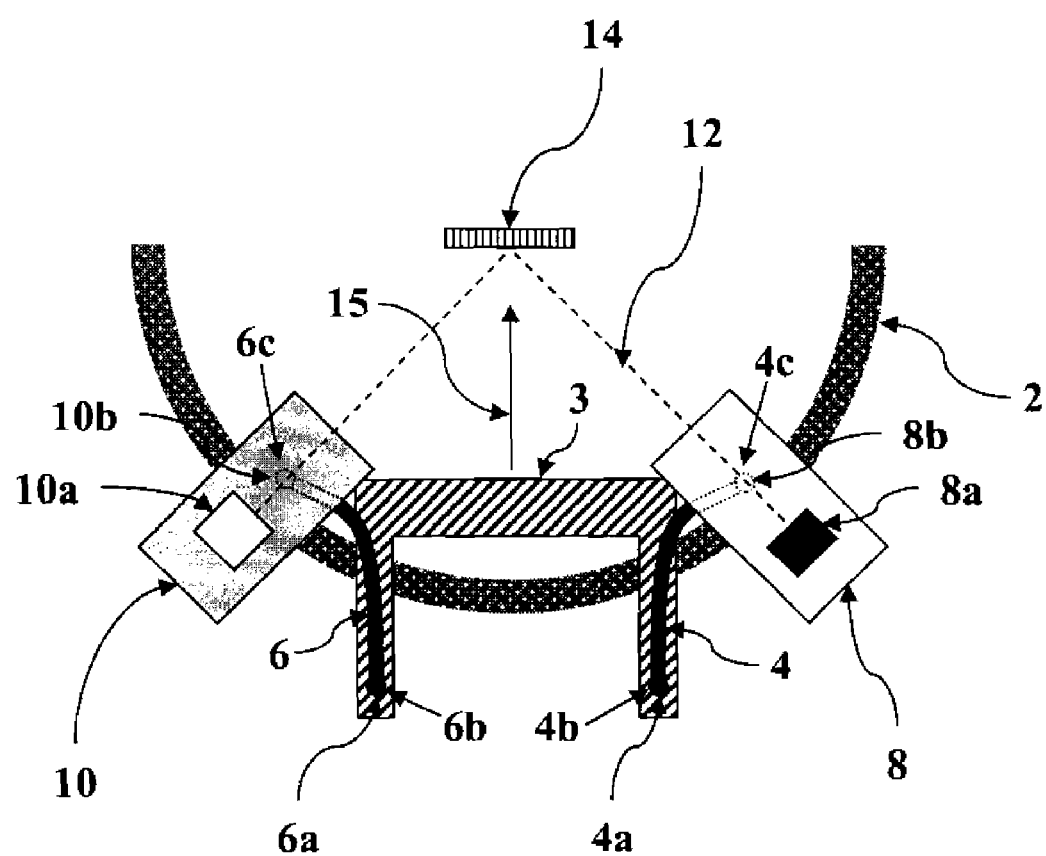
FIG. 2 illustrates another embodiment that includes a driving mechanism.
Figure 3:
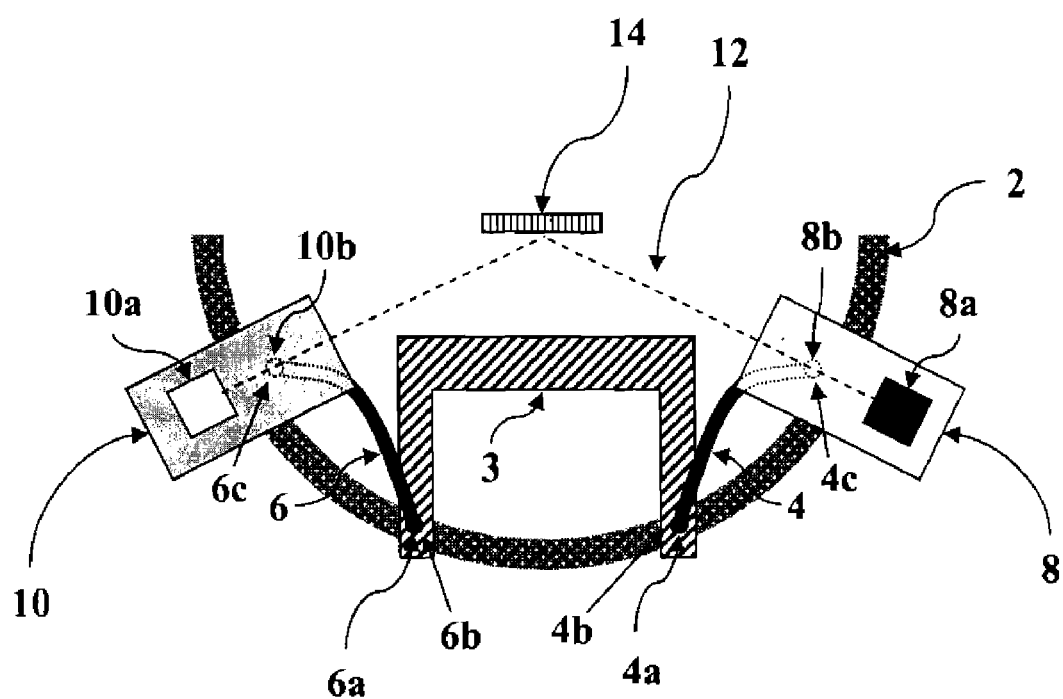
FIG. 3 illustrates the movement of some components in FIG. 2.

In another embodiment, the instrument further comprises a driving mechanism that comprises, referring to FIG. 2: a driving bridge (3) having a first pivot point (4*a*) and a second pivot point (6*a*); a first swing arm (4) with a first end (4*b*) and a second end (4*c*), the first end (4*b*) being connected to the driving bridge (3) through the first pivot point (4*a*); and a second swing arm (6) with a first end (6*b*) and a second end (6*c*), the first end (6*b*) being connected to the driving bridge (3) through the second pivot point (6*a*), wherein the second end (4*c*) of the first swing arm (4) is connected to a pivot point on the light source mount (8*b*) and the second end (6*c*) of the second swing arm (6) is connected to a pivot point on the detector mount (10*b*). Referring to FIGS. 2 and 3, when the driving bridge (3) moves along a path (15) substantially perpendicular to the plane of the sample stage (14), the light source mount (8) and the detector mount (10) move in opposite directions (denoted by arrows 11*a* and 11*b* in FIG. 1).

In one embodiment, the movement of the driving bridge (3) is effected by a linear actuator. In another embodiment, the light source (8*a*) comprises a laser that generates a laser beam. In many embodiments, the laser beam is scanned across the surface of the sample with a microelectromechanical (MEMS) scanner. The MEMS scanner can use a micromirror to reflect and manipulate the light beam path, for example see U.S. Pat. Nos. 6,245,590; 6,362,912; 6,433,907; and 5,629,790. In one embodiment the laser operates at wavelengths from about 360 nm to about 2000 nm. In many embodiments, the detector (10*a*) is a CCD camera. In other embodiments, the instrument further comprises a prism assembly mounted beneath the sample stage (14).

During operation in such a configuration, a prism in the prism assembly is located at the bottom of the sample. The prism assembly and the sample (e.g., a microarray substrate) are made of materials with similar refractive indices and are coupled to each other with an index-matching fluid. Light from the light source (8*a*) passes through one face of the prism, passes through the face of the prism that is coupled to the substrate of the microarray, and reflects off the sample surface (e.g., a gold surface). The reflected light again passes through the face of the prism coupled to the sample substrate, passes through a third face of the prism, and impinges on the detector (10*a*).

In most embodiments, the sample plane is roughly perpendicular to the plane of the semi-circular rail (2). The first swing arm (4) and the second swing arm (6) may be curved. The amount of curvature can depend on many factors including, for example, the distance between the sample (14) and the light source mount (8), the corresponding curvature of the rail (2), and the location of the pivot points (4*b*, 4*c*, 6*b*, and 6*c*). Each of the light source mount (8) and the detector mount (10) can rest, for example, on the semicircular rail (2) through at least two wheels. The light source mount (8) may further include a polarizer. In some embodiments, the instrument includes a routing mirror assembly. The routing mirror assembly can provide flexibility in placing the light source (8*a*) on the light source mount (8). In other embodiments, the detector mount (10) further includes a telescope in the light path (12) between the sample (14) and the detector (10*a*).

Another embodiment is a method, comprising: providing a light source, a detector, and a sample, wherein the light source generates a light beam; directing the light beam at the sample thereby forming an angle of incidence between the light beam and the sample; and moving the light source and the detector substantially synchronously by sliding the light source and detector in opposite directions along a semicircular rail, thereby modifying the angle of incidence. In one embodiment of the method, the sample is a microarray comprising gold and the light beam generates a surface plasmon at the gold surface. Methods and systems for producing microarrays on gold are well known. Microarrays of, for example, nucleic acids, peptides, or proteins covalently or noncovalently bound to a thiol monolayer can be produced on the surface of a gold substrate. The spots on the microarray maybe separated from each other, for example, by hydrophobic areas in cases where the spots are hydrophilic. In many embodiments of the method, the detector is a CCD camera having pixels. One pixel may correspond, for example, to a single spot on the microarray to give a pixel-spot assignment, wherein the pixel-spot assignment does not change as the angle of incidence is modified. Alternatively, a group of pixels of the CCD camera may correspond to a single spot on the microarray, forming a pixel group-spot assignment, wherein the pixel group-spot assignment does not change as the angle of incidence is modified. In another embodiment of the method, at least one linear actuator controls the sliding of the light source and the detector along the semicircular rail.

In all embodiments, the light source can be a laser that forms a laser beam. In many embodiments, the light beam is scanned across the surface of the sample with a frequency. The light beam may be scanned, for example, by using a MEMS scanner as described above. When the light beam is scanned, the rate at which the light source and the detector slide along the rail may be, for example, slower than the frequency of the scan rate such that sample is scanned at least once before the angle of incidence is substantially modified. This means that the detector can be exposed to one or more full scans before the angle of incidence is modified. In many embodiments the light source can include a laser capable of producing light at different wavelengths, for example, from 360 nm to 2000 nm.

Figure 4:
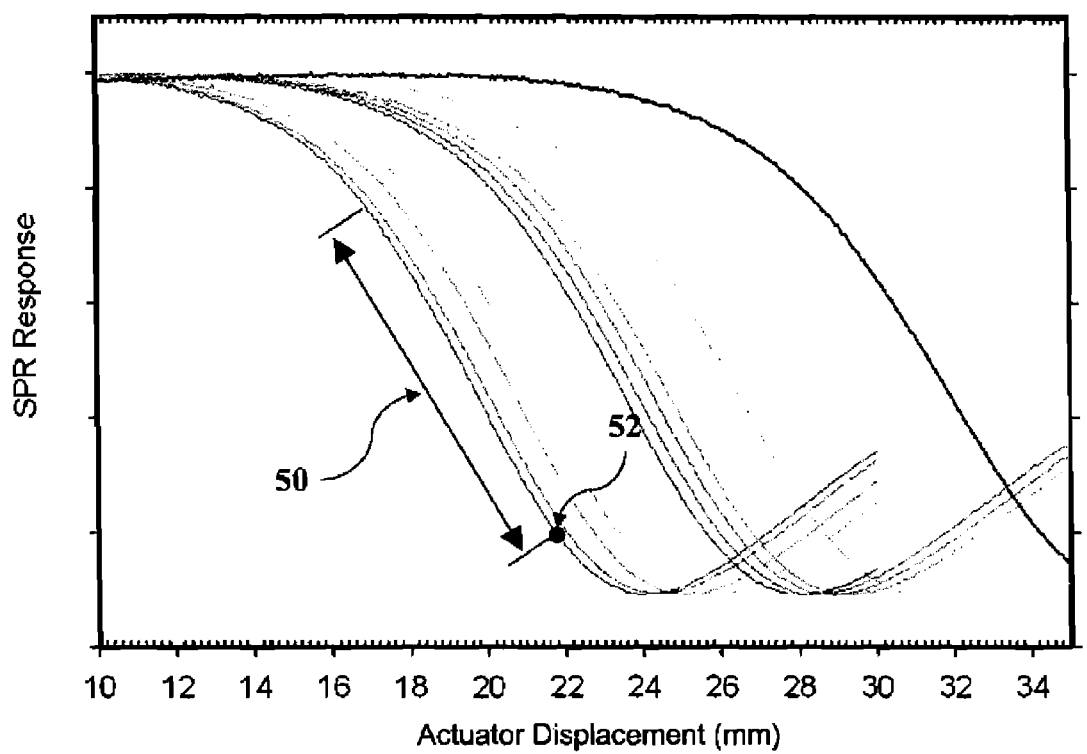
FIG. 4 is a plot of a surface plasmon resonance signal while modifying the angle of incidence.

In many embodiments, the light source is mounted on a light source mount; the detector is mounted on a detector mount; a first swing arm connects the light mount to a driving bridge; a second swing arm connects the detector mount to the driving bridge, and one linear actuator moves the driving bridge in a path perpendicular to a plane where the sample resides. In another embodiment, the method comprises: scanning a region on the microarray to be used in an assay; plotting the intensity of light at the detector against the magnitude of the displacement of the linear actuator to give a curve comprising a linear slope (50 in (FIG. 4)); choosing a specific point on the linear slope; moving the linear actuator to the displacement corresponding to the specific point to give a fixed angle of incidence; and performing the assay at the fixed angle of incidence. In many embodiments, referring to FIG. 4, the point is near the bottom of the linear slope (52).

A number of embodiments of the invention have been described. Nevertheless, it will be understood that various modifications may be made without departing from the spirit and scope of the invention. Accordingly, other embodiments are within the scope of the following claims.

What is claimed:

1. An instrument, comprising:
a semicircular rail;
a sample stage for receiving a sample, the sample stage forming a plane;
a light source mount on the rail;
a light source on the light source mount;
a detector mount on the rail;
a detector on the detector mount;
a driving mechanism, wherein the driving mechanism comprises: a) a driving bridge having a first pivot point and a second pivot point; b) a first swing arm with a first end and a second end, the first end being connected to the driving bridge through the first pivot point; c) and a second swing arm with a first end and a second end, the first end being connected to the driving bridge through the second pivot point, wherein the second end of the first swing arm is connected to a pivot point on the light source mount and the second end of the second swing arm is connected to a pivot point on the detector mount; and
a controller configured to drive the light source mount and the detector mount to move synchronously along the rail in opposite directions through a range of angles, receive a signal from the detector at a plurality of angles within the range, the signal corresponding to surface plasmon resonance responses, select an angle corresponding to a desired surface plasmon resonance response characteristic, and drive the light source mount and the detector mount to the selected angle.

2. The instrument of claim 1, wherein the driving bridge is moved by a linear actuator having a path that is substantially perpendicular to the plane of the sample stage.

3. The instrument of claim 2, wherein the light source comprises a laser that generates a laser beam.

4. The instrument of claim 3, wherein the laser beam is scanned across the surface of the sample with a microelectromechanical mirror.

5. The instrument of claim 3, wherein the laser operates in a wavelength range from about 360 nm to about 2000 nm.

6. The instrument of claim 5, wherein the detector is a CCD camera.

7. The instrument of claim 6, further comprising a prism assembly mounted beneath the sample stage.

8. The instrument of claim 7, wherein the first swing arm and the second swing arm are curved.

9. The instrument of claim 8, wherein the each of the light source mount and the detector mount rests on the semicircular rail through at least two wheels.

10. The instrument of claim 9, wherein the light source mount further includes a polarizer.

11. The instrument of claim 10, wherein the light source mount further includes a routing mirror assembly.

12. The instrument of claim 9, wherein the detector mount further includes a telescope.

13. A method, comprising:
providing a light source, a detector, and a sample comprising a microarray to be used in an assay, wherein the light source generates a light beam;
directing the light beam at the microarray to form an angle of incidence between the light beam and the microarray;
moving the light source and the detector synchronously by sliding the light source and detector in opposite directions along a semicircular rail, thereby modifying the angle of incidence, wherein at least one linear actuator controls the sliding of the light source and the detector along the semicircular rail;
plotting the intensity of light at the detector against the magnitude of the displacement of the linear actuator to give a curve comprising a linear slope;
choosing a specific point on the linear slope;
moving the linear actuator to the displacement corresponding to the specific point to give a fixed angle of incidence; and
performing an assay using the microarray at the fixed angle of incidence;
wherein a) the light source is mounted on a light source mount; b) the detector is mounted on a detector mount; c) a first swing arm connects the light mount to an driving bridge; d) a second swing arm connects the detector mount to the driving bridge, and e) one linear actuator moves the driving bridge in a path perpendicular to a plane where the sample resides.

14. The method of claim 13, wherein the sample is a microarray comprising a gold substrate and the light beam generates surface plasmon resonance at the gold surface.

15. The method of claim 13, wherein the detector is a CCD camera having pixels.

16. The method of claim 13, wherein the light source is a laser.

17. The method of claim 13, wherein the light beam is scanned across the surface of the sample at a selected rate.

18. The method of claim 13, wherein the rate at which the light source and the detector slide along the rail is slower than the frequency of the scan rate such that sample is scanned at least once before the angle of incidence is modified sufficiently to cause a change in a response of the detector arising from the change in the angle of incidence.

19. The method of claim 16, wherein the laser operates in a wavelength range from about 360 nm to 2000 nm.

20. A method, comprising:
1) providing (a) a light source comprising a laser that operates in a wavelength range from about 360 nm to 2000 nm, (b) a detector comprising a CCD camera having pixels, and (c) a microarray comprising a gold substrate to be used in an assay, wherein the light source generates a light beam and the light beam generates surface plasmon resonance at the gold surface,
wherein (i) the light source is mounted on a light source mount; (ii) the detector is mounted on a detector mount; (iii) a first swing arm connects the light mount to a driving bridge; (iv) a second swing arm connects the detector mount to the driving bridge; and (v) a linear actuator moves the driving bridge in a path perpendicular to a plane where the sample resides;
2) directing the light beam at the microarray to form an angle of incidence between the light beam and the microarray;
3) moving the light source and the detector synchronously by sliding the light source and detector in opposite directions along a semicircular rail, thereby modifying the angle of incidence,
wherein at least one linear actuator controls the sliding of the light source and the detector along the semicircular rail;
4) plotting the intensity of light at the detector against the magnitude of the displacement of the linear actuator that controls the sliding of the light source and the detector along the semicircular rail to give a curve comprising a linear slope;
5) choosing a specific point on the linear slope;
6) moving the linear actuator that controls the sliding of the light source and the detector along the semicircular rail to the displacement corresponding to the specific point to give a fixed angle of incidence; and 7) performing an assay using the microarray at the fixed angle of incidence.

21. The method of claim 20, wherein the point is near the bottom of the linear slope.

22. The method claim 15, wherein one pixel corresponds to a single spot on the microarray to give a pixel-spot assignment, wherein the pixel-spot assignment does not change as the angle of incidence is modified.

23. The method of claim 15, wherein a) a group of pixels of the CCD camera corresponds to a single spot on the microarray, forming a pixel group-spot assignment, wherein the pixel group-spot assignment does not change as the angle of incidence is modified.

24. The instrument of claim 1, wherein the desired surface plasmon resonance response characteristic includes a linear relationship between angle and surface plasmon resonance response.

25. The instrument of claim 1, wherein the desired surface plasmon resonance response characteristic includes an out-of-range response from the detector.

* * * * *